(12) United States Patent
Deppeler

(10) Patent No.: US 9,126,302 B2
(45) Date of Patent: Sep. 8, 2015

(54) DEVICE AND METHOD FOR SHARPENING DENTAL CURETTES

(76) Inventor: Arnold Deppeler, Rolle (CH)

( * ) Notice: Subject to any disclaimer, the term of this patent is extended or adjusted under 35 U.S.C. 154(b) by 450 days.

(21) Appl. No.: 13/383,683

(22) PCT Filed: May 4, 2010

(86) PCT No.: PCT/IB2010/001009
§ 371 (c)(1),
(2), (4) Date: Jan. 12, 2012

(87) PCT Pub. No.: WO2011/007217
PCT Pub. Date: Jan. 20, 2011

(65) Prior Publication Data
US 2012/0108145 A1    May 3, 2012

(30) Foreign Application Priority Data

Jul. 16, 2009 (CH) .................................. 1122/09
Jan. 22, 2010 (CH) .................................. 0084/10

(51) Int. Cl.
*B24B 3/60* (2006.01)
*B24B 41/06* (2012.01)
*A61C 3/00* (2006.01)

(52) U.S. Cl.
CPC .............. *B24B 3/605* (2013.01); *B24B 41/066* (2013.01); *A61C 3/00* (2013.01)

(58) Field of Classification Search
CPC ......... B24B 3/605; B24B 19/16; B24D 15/06
USPC .................... 451/6, 9, 15, 279, 359
See application file for complete search history.

(56) References Cited

U.S. PATENT DOCUMENTS

| | | | | | |
|---|---|---|---|---|---|
| 1,411,713 | A | * | 4/1922 | Downing | 451/320 |
| 2,544,097 | A | * | 3/1951 | Lentz | 451/369 |
| 2,578,309 | A | * | 12/1951 | Kroczek | 451/278 |
| 2,911,771 | A | * | 11/1959 | Amiet | 451/375 |

(Continued)

FOREIGN PATENT DOCUMENTS

| | | |
|---|---|---|
| CH | 683 505 | 3/1994 |
| DE | 40 10 635 | 6/1991 |

(Continued)

OTHER PUBLICATIONS

International Search Report dated Aug. 13, 2010, corresponding to PCT/IB2010/001009.

*Primary Examiner* — Maurina Rachuba
(74) *Attorney, Agent, or Firm* — Young & Thompson

(57) ABSTRACT

A device for sharpening one or more cutting edges of a dental curette has a base support with a frame articulated thereon, and at least one sharpening guide. The frame supports a grinding wheel rotationally driven by a motor and a sharpening guide support intended to receive the sharpening guide(s). The guide includes at least one indicator in the form of a line marked on the guide, whose angle with the horizontal being between 10° and 50° but preferably equal to 10°, 20° or 30° and corresponding to the type of dental curette to be sharpened. The sharpening guide(s) can move with respect to the support, and the support and/or the guide include(s) indexing and positioning elements determining indexing positions of the guide on the support, each indexing position corresponding to a different indicator. A method of sharpening one or more cutting edges, and a sharpening guide are described.

19 Claims, 6 Drawing Sheets

(56) References Cited

U.S. PATENT DOCUMENTS

| | | | |
|---|---|---|---|
| 3,069,814 A * | 12/1962 | Malpas et al. | 451/165 |
| 3,098,327 A * | 7/1963 | Malin | 451/278 |
| 4,259,814 A * | 4/1981 | Glaser et al. | 451/273 |
| 4,509,268 A * | 4/1985 | Marquam et al. | 33/201 |
| 4,821,462 A * | 4/1989 | Moore | 451/555 |
| 5,155,939 A * | 10/1992 | Pheulpin | 451/162 |
| 5,197,227 A | 3/1993 | Svanberg | |
| 5,331,774 A * | 7/1994 | Domenella | 451/45 |
| 5,655,957 A * | 8/1997 | Lystager | 451/278 |
| 5,816,893 A | 10/1998 | Kangasniemi | |
| 5,934,975 A * | 8/1999 | Svanberg | 451/11 |
| 6,142,856 A * | 11/2000 | Romhild | 451/279 |
| 6,146,257 A * | 11/2000 | Himeno et al. | 451/321 |

FOREIGN PATENT DOCUMENTS

| | | |
|---|---|---|
| EP | 0 694 368 | 1/1996 |
| EP | 0 919 327 | 6/1999 |
| WO | 92/09403 | 6/1992 |

\* cited by examiner

DEVICE AND METHOD FOR SHARPENING DENTAL CURETTES

BACKGROUND OF THE INVENTION

1. Field of the Invention

The present invention relates to a device and a method for sharpening dental curettes.

Sharpening dental tools is problematic in that it must be able to be performed regularly by the operator or his assistants and must be precise and uniform.

2. Description of the Related Art

Manual sharpening devices for dental curettes are known, such as the Kramer sharpener or the device described in document CH 683 505, and motorised devices are known, such as the "Hawe PerioStar 3000" (trademark) from Kerr Hawe, the "LM Rondo Plus" from LM Dental Oy, or the "Sidekick" (trademark) from Hu-Friedy.

It often takes longer and is more complex to uniformly and precisely sharpen a cutting edge of a dental curette using manual devices. These devices require a great amount of dexterity and precision on the part of the operator in the placement and movements imparted to the curette. The motorised devices are easier to use but still require precise positioning of the curette with respect to the sharpening stone.

BRIEF SUMMARY OF THE INVENTION

The present invention relates to a device and method for sharpening dental curettes which are simple, less costly, easy to implement by the operator or his assistants and which permit precise and simple positioning of a dental curette to be sharpened in order to achieve precise and uniform sharpening of the cutting edge(s) of said curette. The present invention also relates to a sharpening guide for implementing the sharpening method using said device.

The device and the method for sharpening dental curettes in accordance with the invention are characterised by the features listed in claim 1 and claim 16 respectively. The sharpening guide for implementing said sharpening method is for its part characterised by the features listed in claim 19.

In particular, in one preferred embodiment of the invention, the device comprises a magnifying lens in line with the grinding wheel providing a magnification of the sharpening area and thus permitting precise and easy positioning of a dental curette to be sharpened by the operator.

BRIEF DESCRIPTION OF THE DRAWINGS

The accompanying drawings schematically illustrate, by way of a non-limiting example, several embodiments of the device for sharpening dental curettes in accordance with the invention for the implementation of the method for sharpening such curettes in accordance with the invention.

DETAILED DESCRIPTION OF THE PREFERRED EMBODIMENTS

Figure 1:
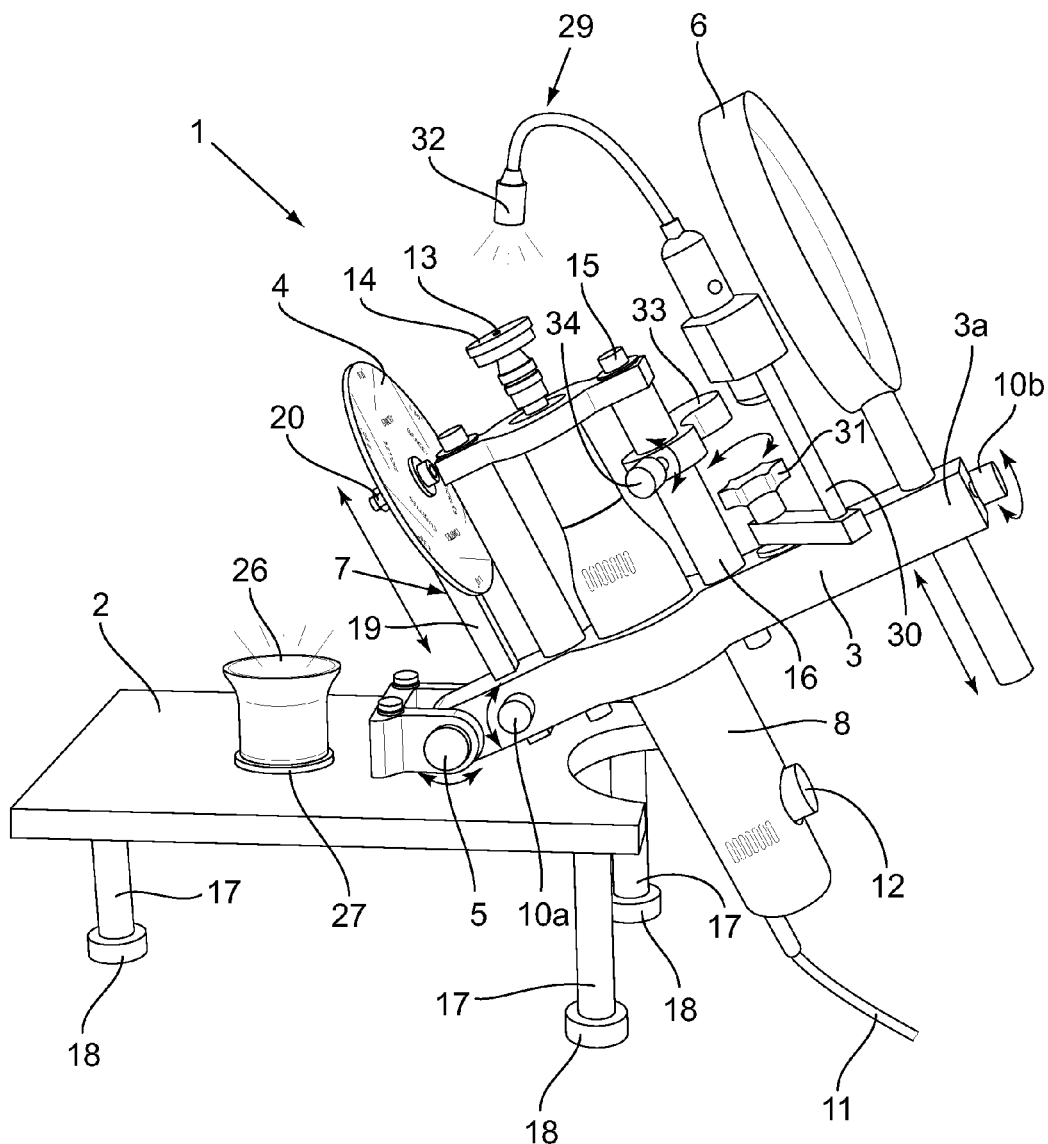
FIG. 1 is a side view of a first embodiment of the device in accordance with the invention.

A first embodiment of the device in accordance with the invention will now be described with reference to FIGS. 1 to 3. The sharpening device 1 for dental curettes in accordance with the invention, shown in a first embodiment in FIG. 1, has a base plate 2 on which there is articulated a frame 3 and at least one sharpening guide 4.

Preferably, the inclination of the frame 3 with respect to the base plate 2 is adjustable using a first adjustment screw 5 for example.

The frame 2 supports a magnifying lens 6, a sharpening guide support 7 as well as a motorised grinder 8.

The magnifying lens 6 is fixed to the free end 3a of the frame 3. The axis of the magnifying lens 6 and the axis of the guide support 7 are preferably perpendicular to the axis of the frame 3. Second adjustment screws 10a, 10b enable the height of the guide support 7 and of the magnifying lens 6 respectively to be adjusted with respect to the frame 3.

The grinder 8 as illustrated in FIG. 1 comprises an electrical connecting cable 11, a trigger 12 and a mandrel 13 intended to receive a grinding wheel 14. Preferably, the grinding wheel 14 has a cylindrical flat form and the active surface of the grinding wheel 14 is parallel to the axis of the frame 3.

Preferably, the mandrel 13 and the grinding wheel 14 are designed such that the grinding wheel 14 is press-fitted to the mandrel 13 and can be removed from said mandrel 13 using neither an unscrewing process nor another tool. It is thus easier to change the grinding wheel and it is very easy to simply turn over the grinding wheel 14 when one surface thereof is worn for example.

The grinding wheel 14 could be of a different size, shape or abrasive grain and the grinder 8 could further comprise a speed regulator or even be battery-operated.

The grinder 8 is placed on the frame 3 between the magnifying lens 6 and the guide support 7 and the axis of the grinding wheel 14 is preferably perpendicular to the axis of the frame 3. Preferably, and as illustrated in FIG. 1, the grinder 8 is fixedly attached to the frame 3 by locking screws 15 and a secondary frame 16.

The sharpening device 1 in accordance with the invention is intended to be placed on a table or any other working surface. For ease of use, the base plate 2 preferably comprises feet 17. Said feet 17 could be height-adjustable. For safe and suitable gripping of the device, the feet preferably comprise anti-slip pads 18. This device could comprise any other suitable fixing means such as a clamp for example.

The sharpening guide support 7 is formed in this first embodiment by a rod 19 whose height can be adjusted with respect to the frame 3. The rod 19 supports a rotating guide disk 4 fixed to said rod 19 using a screw 20 for example. The guide disk 4 is freely rotatable with respect to the rod 19. Indexing means are provided to determine the different usage positions of the guide disk during rotation thereof. Preferably, these indexing means comprise a protrusion (not shown) provided on the rod 19 and co-operating with at least one but preferably six recesses 21 in the rear face 4b of the guide disk as shown in FIGS. 2 and 3.

Figure 2:
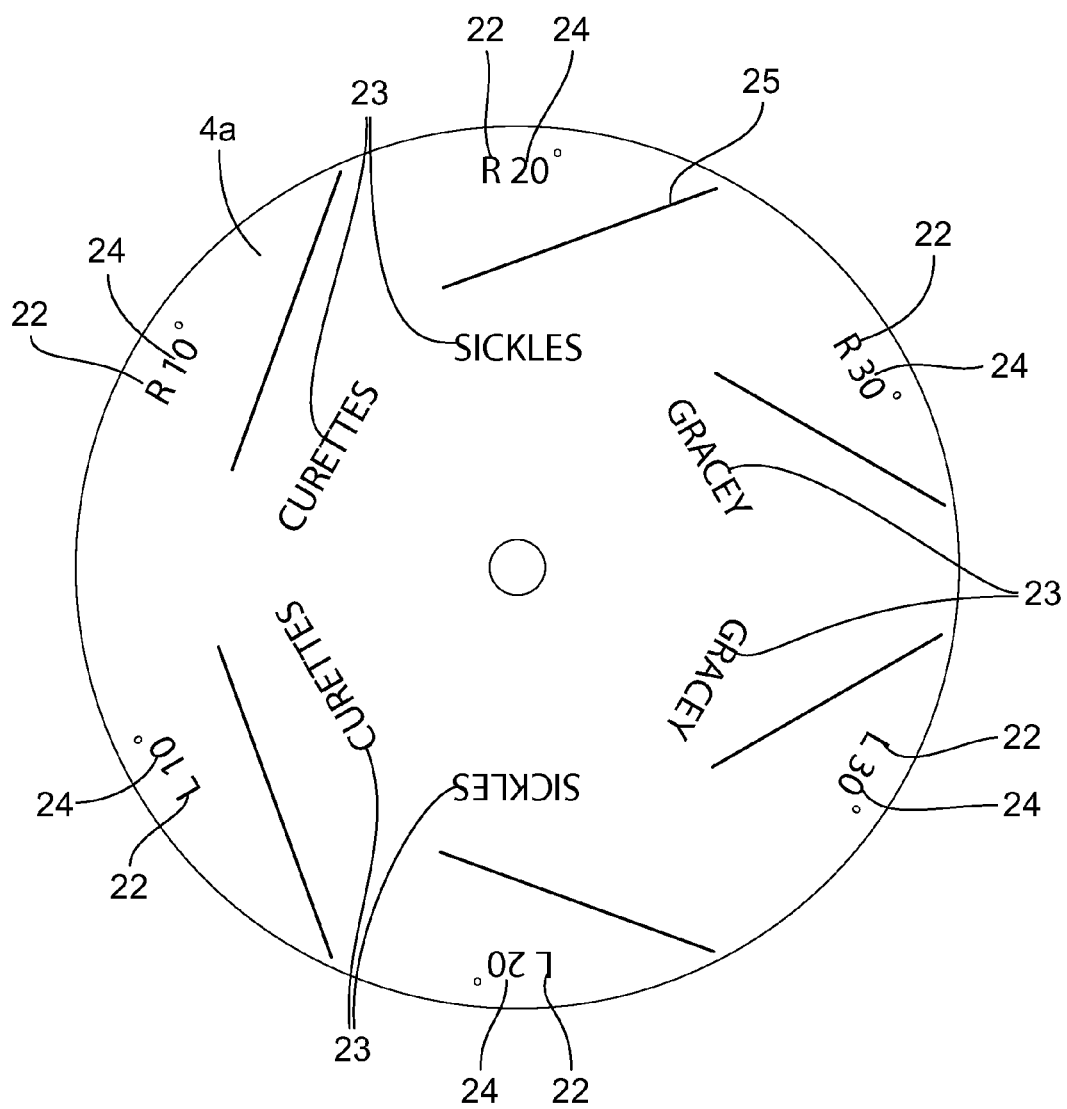
FIGS. 2 and 3 are front and rear views respectively of a sharpening guide of the sharpening device illustrated in FIG. 1.
Figure 3:
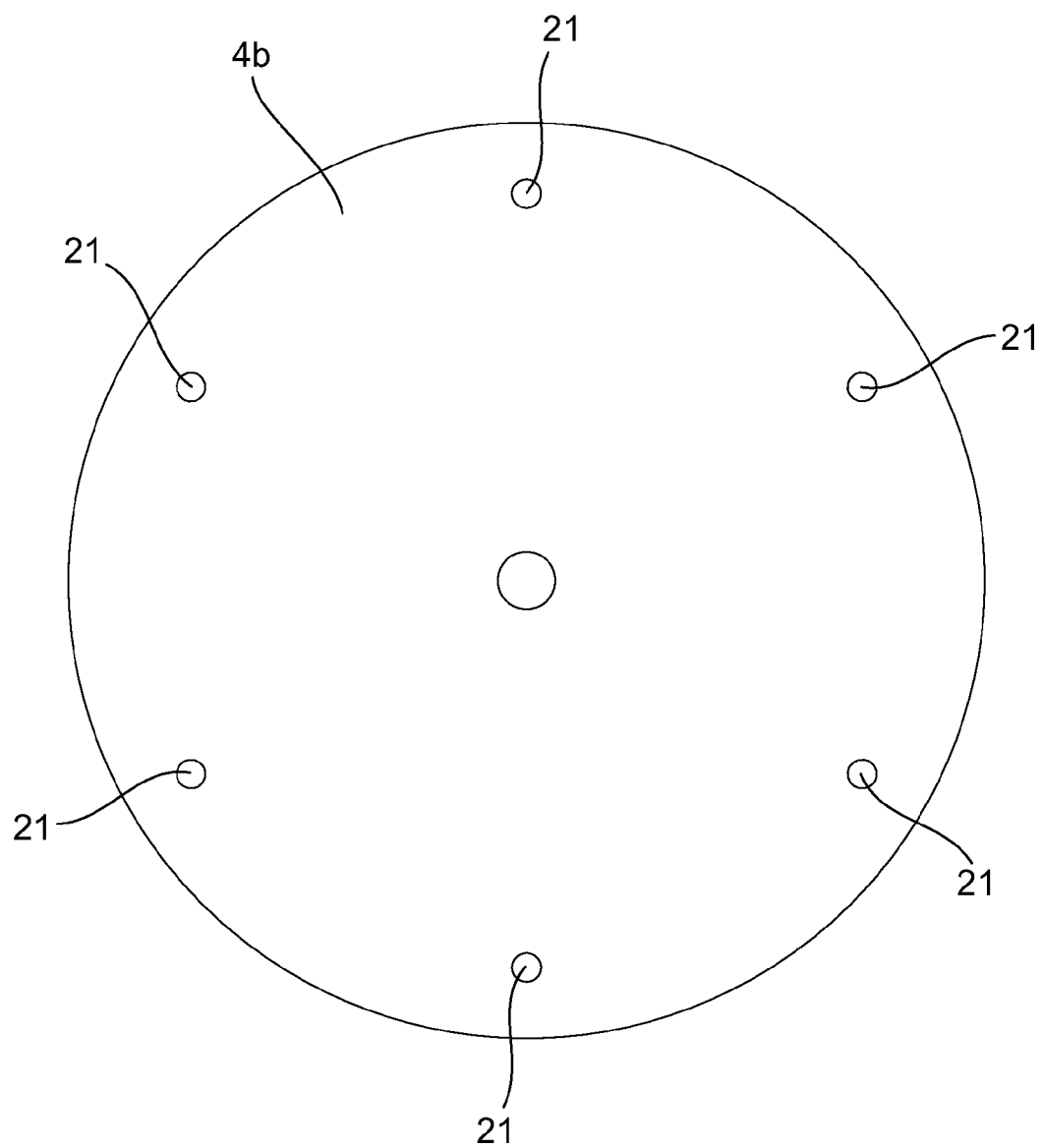

The guide disk is divided into at least one but preferably six sectors on its front face 4a shown in FIG. 2. Each indexing position of the guide disk is determined by a recess 21 and corresponds to a sector. The recesses 21 and the sectors are designed such that the correct position for each sector with respect to the grinding wheel 14 is ensured when snap-fitting the protrusion of the guide support 7 into the recess 21 corresponding to said sector.

Each of the sectors of the guide disk 4 comprises an indicator formed preferably of four markings:

the first marking 22 is the letter R or L and indicates that said sector is intended to be used as a guide for a right-handed or left-handed operator respectively.

the second marking 23 contains the name of the type of curette to which the sector corresponds. There are three types of dental curettes: universal curettes, scalers (sickles) and Gracey-type curettes.

the third marking 24 designates the respective angles 10°, 20° and 30° corresponding to the different types of curette: 10° corresponding to the universal curettes, 20° to the scalers (sickles) and 30° to the Gracey-type curettes.

the fourth marking 25 is an indicating line, the angle of which with the horizontal corresponding to the angle of the third marking (the angles and orientations of the markings are defined for each sector in its indexing position). It is this line which will be used as a guide for the operator during sharpening. As illustrated in FIG. 2, the inclination of the indicating line also depends upon the laterality of the guide, i.e., upon the first marking 22: if said sector is intended to be used as a guide for a right-handed operator, the indicating line rises from left to right from the point of view of the operator. If said sector is intended to be used as a guide for a left-handed operator, the indicating line then falls from left to right from the point of view of the operator.

Thus, a single guide disk 4 allows three different types of curette to be sharpened, whatever the laterality of the operator.

As a variation, the device could comprise two guide disks 4, one for right-handed operators and one for left-handed operators. Each disk would then be divided into three sectors, one for each type of curette, each sector having an indicator formed of the second 23, third 24 and fourth 25 markings described above. The rear face of such disks then comprises three recesses 21, each corresponding to a sector and allowing the disk to be positioned by means of a snap-fitting arrangement with the protrusion of the guide support 7.

Preferably, and as illustrated in FIG. 1, the sharpening device in accordance with the invention further comprises an eyepiece 26 stored in a storage mount 27 provided for this purpose on the base plate 2. The eyepiece 26 enables the result of the sharpening operation to be verified after it is completed.

Preferably, the device in accordance with the invention further comprises an illumination system 29 allowing the grinding wheel 14 and the sharpening area of the dental curette to be sharpened to be illuminated. In the embodiments described in the Figures, the illumination system 29 comprises a hinged arm 30 fixed to the frame 3 between the magnifying lens 6 and the grinder 8 using a fixing screw 31 and preferably having a light-emitting diode (LED) lamp 32. The hinged arm 30 can be pivoted with respect to the frame in order to position the illumination system in a suitable manner depending upon whether the operator is right-handed or left-handed.

Preferably, the device in accordance with the invention further comprises a stabilising support 33 fixed to the secondary frame 16, the lateral and height position of which on said frame being adjustable using a third adjustment screw 34 for example. Said stabilising support 33 is designed to provide a support platform for the hand of the operator when sharpening a dental curette. The hand of the operator is thus stabilised and possible shaking is minimised, ensuring an even greater degree of precision when sharpening the dental curette.

Figure 4:
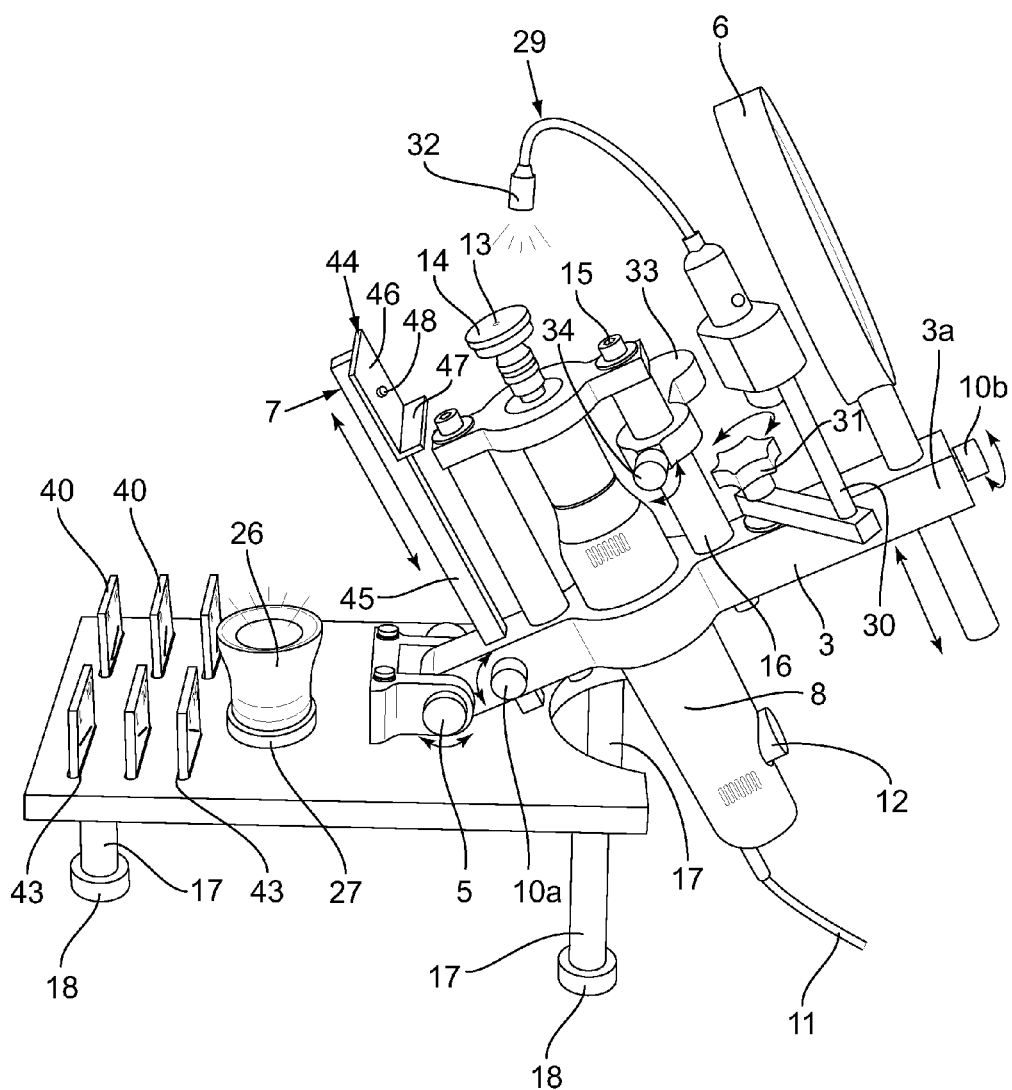
FIG. 4 is a side view of a second embodiment of the device in accordance with the invention.
Figure 5:
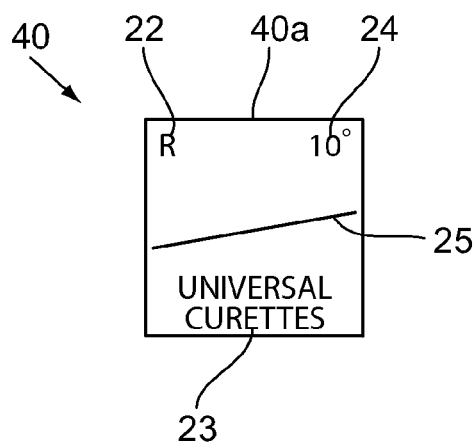
FIGS. 5 and 6 are front and rear views respectively of a sharpening guide of the sharpening device illustrated in FIG. 4.
Figure 6:
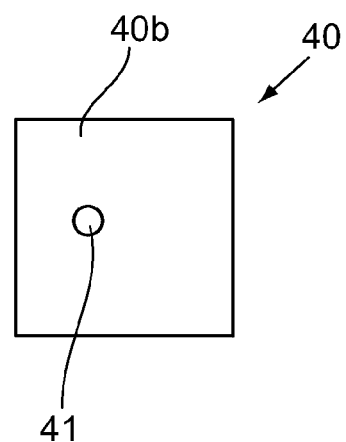

A second embodiment of a device for sharpening dental curettes in accordance with the invention will now be described with reference to FIGS. 4 to 6. In this embodiment, the guide disk 4 is replaced by at least one but preferably six sharpening guides 40. The sharpening guides 40 are in the form of a rectangular plate. The rear face 40b of each of the sharpening guides 40, which is shown in FIG. 6, has a recess 41 whose position varies depending upon the guides. The role and said position of the recess 41 will be explained hereinafter. The front face 40a of each of the guides, which is shown in FIG. 5, has markings which will also be explained hereinafter.

In this embodiment, the base plate 2 has second storage mounts 43 which are each intended to receive a sharpening guide 40 in a vertical position. The presence of said storage mounts 43 thus facilitates the storage of the sharpening guides 40 as well as their accessibility for the operator.

The storage mounts 43 could be replaced by any other storage system, whether fixed to the base plate 2 or not. Thus, the sharpening device could comprise a housing used to store the sharpening guides 40.

The frame 3 supports, as in the first embodiment, a magnifying lens 6, a sharpening guide support 7 as well as a motorised grinder 8.

In this embodiment, the sharpening guide support 7 has the shape of a rest 44 comprising a leg 45 and a tray 46 provided with a shoulder 47 intended to receive a sharpening guide 40. The tray 46 has a protrusion 48 intended to co-operate with the recess 41 in each of the sharpening guides 40. The correct positioning of a sharpening guide 40 on the tray 46 is ensured when snap-fitting the protrusion 48 into the recess 41 in said guide and by the shoulder 47 preventing the guide from pivoting. Of course, the sharpening guides 40 could conversely comprise a protrusion on their rear face which then co-operates with a recess in the tray of the rest.

The protrusion 48, the recess 41 and the shoulder 47 of the rest 44 thus form positioning means for the sharpening guides 40 on the rest 44. In general, these positioning means could be formed by any other suitable element and the rest 44 does not have to comprise a shoulder 47.

There are four markings on the front face 40a of each sharpening guide 40 shown in FIG. 5, these markings being similar to those shown on each sector of the guide disk 4 described in the first embodiment of the invention:

the first marking 22 is the letter R or L and indicates that the guide is intended to be used by a right-handed or left-handed operator respectively.

the second marking 23 contains the name of the type of curette to which the guide corresponds.

the third marking 24 designates the respective angles 10°, 20° and 30° corresponding to the different types of curette: 10° corresponding to the universal curettes, 20° to the scalers (sickles) and 30° to the Gracey-type curettes.

the fourth marking 25 is an indicating line, the angle of which with the horizontal corresponding to the angle of the third marking 24. It is this line which will be used as a guide for the operator during sharpening. As illustrated in FIG. 5, the inclination of the indicating line also depends upon the laterality of the guide, i.e., upon the first marking: if the guide is intended for a right-handed user, the indicating line rises from left to right from the point of view of the operator. If the guide is intended for a left-handed user, the indicating line falls from left to right from the point of view of the operator.

The position of the recess 41 on the rear face 40b of each sharpening guide 40 also depends upon the type of dental curette to which the guide corresponds as well as the laterality of said guide.

The other components of the device in accordance with the second embodiment, such as the magnifying lens 6, the illumination system 29, the stabilising support 33 and the grinder 8 are similar to those described in the first embodiment in every respect.

Figure 8:
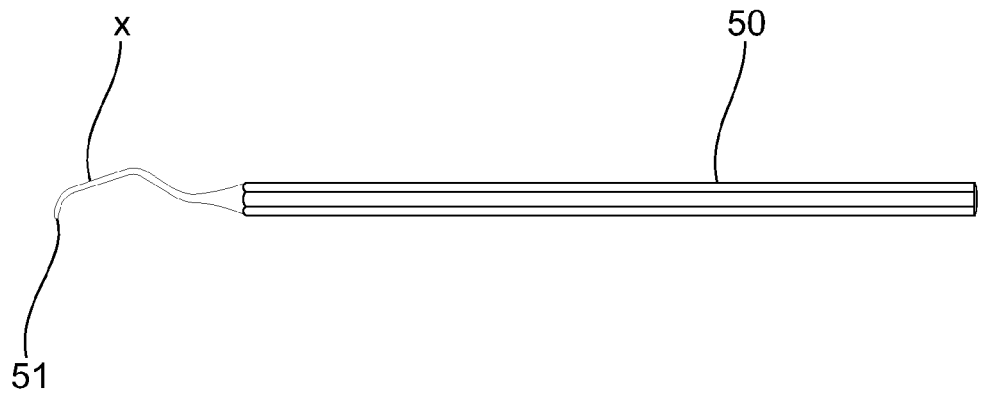
FIG. 8 illustrates a dental curette.
Figure 7:
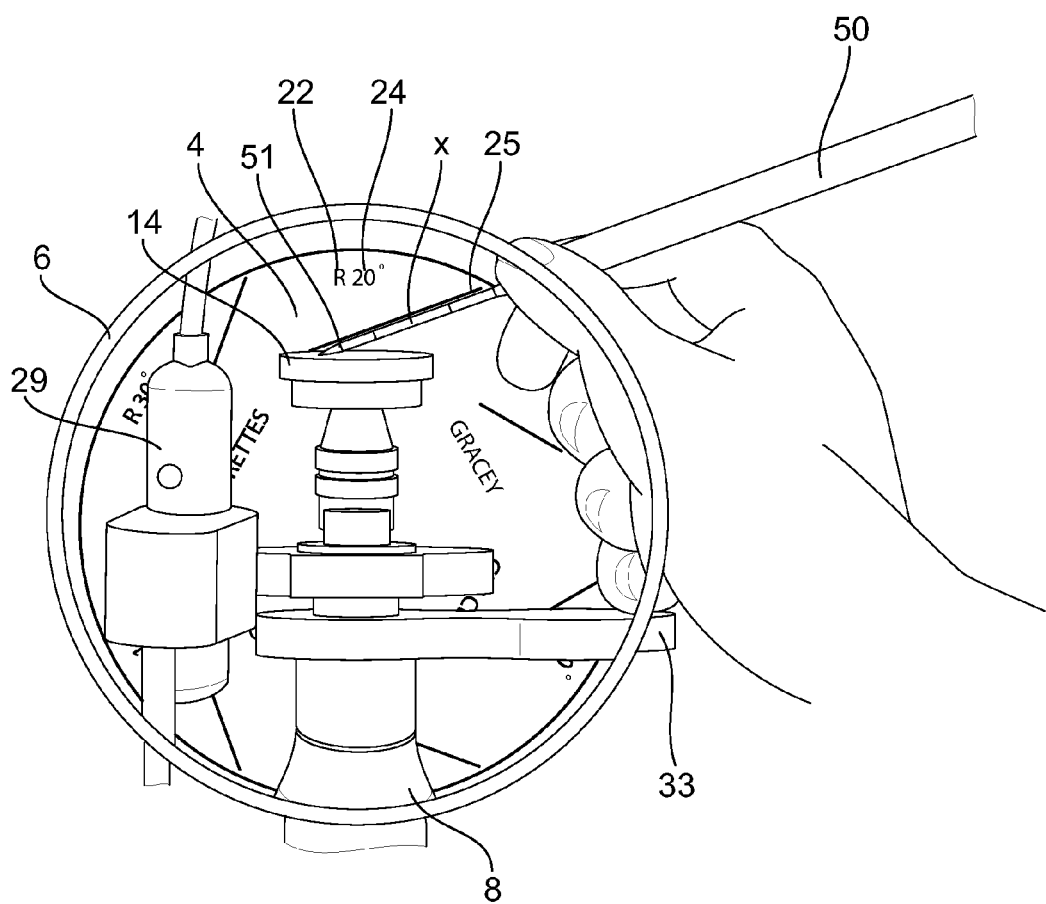
FIG. 7 is a view of the device illustrated in FIG. 1 during use thereof by a practitioner for sharpening a dental curette.

The method of sharpening dental curettes in accordance with the invention implemented using a device for sharpening dental curettes in accordance with the first embodiment will now be described with reference to FIG. 7 and has the following steps:

1. The operator adjusts the inclination of the frame 3 with respect to the base plate 2, the height of the guide support 7 and of the magnifying lens 6 as well as the position of the illumination system 29 and of the stabilising support 33 in accordance with his height, his laterality, the height of the chair and/or the table on which the device is placed.
2. The operator selects a sector of the guide disk 4 corresponding to the type of dental curette 50 to be sharpened, illustrated in FIG. 8, and to the laterality of the operator and causes the guide disk 4 to pivot until said sector is suitably positioned. Said sector is correctly positioned when the protrusion of the guide support 7 co-operates with the recess 21 of the rear face 4b of the disk 4 corresponding to the selected sector.
3. The curette to be sharpened is manually held by the operator who applies the edge 51 to be sharpened onto the grinding wheel 14 whilst aligning the last straight part x of the curette 50 on the line 25 marked on the sharpening guide.
4. The grinder 8 is started using the trigger 12. Whilst keeping the straight part x of the curette 50 aligned with the line 25 of the guide and the edge 51 to be sharpened supported against the grinding wheel 14, the operator simultaneously imparts a rotational movement to the handle of the curette 50 on an axis coinciding with said handle to follow the curve of the edge 51 to be sharpened. This operation is greatly facilitated owing to the magnification provided by the magnifying lens 6 thus permitting extremely precise positioning and sharpening.
5. The operator monitors the result of the sharpening using the eyepiece 26 placed on the base plate 2 of the device.

The method of sharpening dental curettes in accordance with the invention implemented using a device for sharpening dental curettes in accordance with the second embodiment is similar to the above-described method except that step 2 is replaced by the following step:

2': The operator places a sharpening guide 40 corresponding to the type of dental curette 50 to be sharpened, illustrated in FIG. 8, and to the laterality of the operator onto the rest 44. The sharpening guide 40 is correctly positioned when the protrusion 48 of the tray 46 of the rest 44 co-operates with the recess 41 in the rear face 40b of the guide 40.

By providing a suitable mode of operation, this device may also be used to sharpen excavators, small operating scissors or other instruments which require sharpening.

The magnifying lens 6 enables the operator to easily and precisely position the dental curette to be sharpened with respect to the corresponding guide. The magnifying lens preferably has a diameter of 100 mm and thus also acts as a protective screen between the grinding wheel and the operator.

The described device is simple and is characterised by extremely safe usage, an extremely quick positioning of the tool, an extremely fine cutting surface state, precise sharpening and a working position which is comfortable and suitable for everyone.

The invention claimed is:

1. A device for sharpening one or more cutting edges of a dental curette, the sharpening device comprising:
    a base support on which there is articulated a frame supporting a grinding wheel rotationally driven by a motor and a sharpening guide support; and
    at least one sharpening guide, the sharpening guide support being configured to receive the sharpening guide, the sharpening guide comprises a plurality of indicators, each of the indicators being a line marked on the sharpening guide, the angle of the line with respect to a horizontal line being between 10° and 50° but preferably equal to 10°, 20° or 30° and corresponding to a type of dental curette to be sharpened, the sharpening guide being configured to move with respect to the sharpening guide support,
    wherein the sharpening guide support and/or the sharpening guide comprise indexing and positioning means determining indexing positions of the sharpening guide on the sharpening guide support, each indexing position corresponding to a different one of the indicators,
    the sharpening guide is a visual guide only, and
    the sharpening guide has a central axis that extends perpendicular to the axis of the grinding wheel.

2. The device as claimed in claim 1, wherein the frame supports a magnifying lens on its free end, and
    the grinding wheel is located between the sharpening guide support and the magnifying lens.

3. The device as claimed in claim 1, wherein the inclination of the frame with respect to the base support is adjustable.

4. The device as claimed in claim 1, wherein the height of the sharpening guide support with respect to the frame is adjustable.

5. The device as claimed in claim 2, wherein the height of the magnifying lens with respect to the frame is adjustable.

6. The device as claimed in claim 1, wherein the indexing and positioning means comprise at least one recess in a rear face of the sharpening guide cooperating with a protrusion on the sharpening guide support.

7. The device as claimed in claim 1, wherein the line marked on the sharpening guide and forming the indicator one of rises from left to right and is adapted to a right-handed user, and falls from left to right and is adapted to a left-handed user.

8. The device as claimed in claim 1, wherein the sharpening guide is a disk pivotably mounted on the sharpening guide support along an axis perpendicular to the axis of the grinding wheel.

9. The device as claimed in claim 8, wherein the disk has six different indicators, each of the indicators being a line, the angle of the line with respect to a horizontal line being one of 10°, 20°, and 30°, the first three lines rising from left to right and being adapted to a right-handed user and the second three lines falling from left to right and being adapted to a left-handed user,
    wherein the indexing and positioning means is configured to determine six positions of the disk with respect to the sharpening guide support, each of positions corresponding to a different one of the indicators.

10. The device as claimed in claim 1, further comprising a first set of three sharpening guides, each of the first set of sharpening guides having a line, the angle of the line with respect to a horizontal line being 10°, 20°, and 30°, respectively.

11. The device as claimed in claim 10, further comprising a second set of three sharpening guides, each of the second set of sharpening guides having a line, the angle of which with the horizontal being 10°, 20° and 30° respectively, the respective lines of the guides of one of the first and second sets rising from left to right and thus being adapted to a right-handed user, whereas the respective lines of the guides of the other one of the first and second sets falling from left and right and thus being adapted to a left-handed user.

12. The device as claimed in claim 1, further comprising an eyepiece configured to monitor the result of the sharpening.

13. The device as claimed in claim 1, further comprising a grinding wheel mounted on a mandrel so as to be detachable manually without the need for a tool.

14. The device as claimed in claim 3, further comprising an illumination system mounted on the frame between the magnifying lens and the grinding wheel, the position of the illumination system on said frame being adjustable.

15. The device as claimed in claim 3, further comprising a stabilizing support mounted on the frame between the magnifying lens and the grinding wheel, the position of the stabilizing support on said frame being adjustable and the stabilizing support being designed to provide a support for the hand of the user during sharpening of a dental curette using said device.

16. A method of sharpening a dental curette using the device as claimed in claim 1, the method comprising:

positioning the sharpening guide in one of the indexing positions corresponding to a selected one of the indicators on the sharpening guide support, the indicator being marked on the sharpening guide and corresponding to the type of the curette to be sharpened and/or to the laterality of the practitioner, the indexing position being defined with respect to the sharpening guide support by the indexing and positioning means shown on the sharpening guide support and/or the sharpening guide, wherein an edge of the curette to be sharpened is applied against the grinding wheel while a last straight part of the curette directly adjacent to the edge of the curette is aligned with the line marked on the guide and forming the selected indicator without the guide and the curette coming into physical contact with each other, and the grinding wheel is rotated.

17. The method as claimed in claim 16, further comprising:
adjusting the inclination of the frame with respect to the base support, the height of the sharpening guide support, the height of a magnifying lens supported by the frame, and the position of an illumination system supported by the frame, and the position of a stabilizing support of the frame, with respect to the frame.

18. The method as claimed in claim 16, wherein an oscillating angular movement is imparted to the curette about the axis of the handle of the curette in accordance with the curvature of the edge while maintaining the edge against the grinding wheel and the last straight part of the curette aligned with the line marked on the guide and forming the selected indicator.

19. The device as claimed in claim 2, wherein the inclination of the frame with respect to the base support is adjustable.

* * * * *